United States Patent [19]

Glass

[11] 4,387,706
[45] Jun. 14, 1983

[54] IRIS RETRACTOR

[76] Inventor: Robert M. Glass, 1173 Staffler Rd., Bridgewater, N.J. 08807

[21] Appl. No.: 252,951

[22] Filed: Apr. 10, 1981

[51] Int. Cl.³ .............................................. A61B 17/02
[52] U.S. Cl. ....................................... 128/20; 128/341
[58] Field of Search .................. 3/1.5, 13; 128/18, 20, 128/3, 12, 132, 249, 269, 303 R, 341, 343; 285/412

[56] References Cited

U.S. PATENT DOCUMENTS

| | | | |
|---|---|---|---|
| 2,374,574 | 4/1945 | Adams | 285/412 |
| 3,579,642 | 5/1971 | Heffernan et al. | 3/1.5 |
| 3,711,870 | 1/1973 | Deitrick | 3/13 |
| 4,321,916 | 3/1982 | McKee | 128/20 |

FOREIGN PATENT DOCUMENTS 114051  3/1918  United Kingdom .................. 128/20

Primary Examiner—Kyle L. Howell
Assistant Examiner—Max F. Hindenburg
Attorney, Agent, or Firm—Lawrence E. Sklar

[57] ABSTRACT

An iris retractor for use during eye surgery. The retractor comprises a substantially circular, resilient ring, the ring having an arcuate flange extending downwardly and outwardly therefrom, a plurality of transverse, reinforcing struts extending across the ring and the arcuate flange, and a pair of opposing pinions situated on the flange of the substantially circular, resilient ring. The retractor, prior to being placed within the pupil, may be contracted into a substantially oval configuration by means of suitable forceps engaging the opposing pinions, and, when placed within the pupil, may be expanded back into its circular configuration by means of the resiliency within the retractor.

6 Claims, 5 Drawing Figures

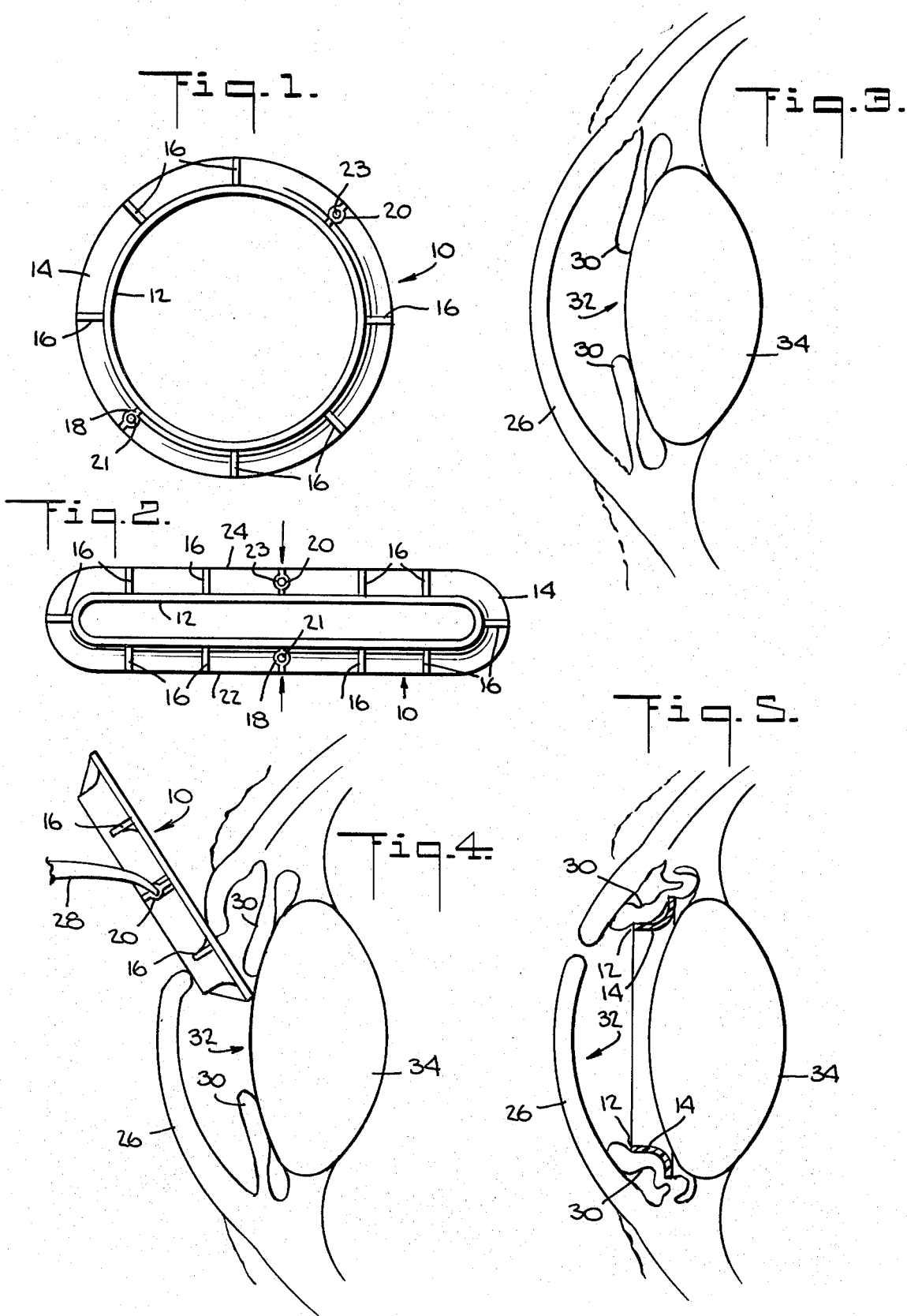

IRIS RETRACTOR

BACKGROUND OF THE INVENTION

The instant invention relates to an iris retractor for increasing the pupillary aperture during eye surgery.

One of the major problems in cataract surgery, extracapsular or intracapsular, with or without implantation of an intraocular lens, is the size of the pupil. The increased intraocular manipulation which accompanies these new procedures is usually attended by constriction of the pupil, which makes visualization of the posterior lens capsule and the capsular fornities quite difficult. Dilute solutions of epinephrine are presently used to increase the pupillary aperture, but these solutions are not without their toxicity and side effects.

There are devices being used in eye surgery today which retract the iris, thereby enlarging the pupil, but these retractors must be held by someone, such as a surgeon or a nurse. Furthermore, the iris retractors currently in use do not provide equal stretching for 360 degrees around the iris.

The instant invention overcomes the foregoing problems by providing an iris retractor which is held in place by suitably designed forceps and which provides equal stretching for 360 degrees around the iris.

SUMMARY OF THE INVENTION

The instant invention provides an iris retractor for use during eye surgery. The retractor comprises a substantially circular, resilient ring having an arcuate flange co-extensive therewith extending outwardly therefrom, a plurality of transverse, reinforcing struts extending from the ring across the arcuate flange, and a pair of opposing pinions situated on the flange of the substantially circular, resilient ring and co-linear with the center of the ring. The retractor, prior to being placed within the pupil, may be contracted into a substantially oval configuration by means of suitable forceps engaging the opposing pinions, and, when placed within the pupil, may be expanded back into its circular configuration by means of the resiliency within the retractor.

BRIEF DESCRIPTION OF THE DRAWINGS

FIG. 1 is a top plan view of an iris retractor according to the instant invention as it would appear long prior to and after insertion into the pupil;

FIG. 2 is a top plan view of the retractor seen in FIG. 1 contracted into an oval configuration immediately prior to insertion into the pupil;

FIG. 3 is a side elevational view of the iris and surrounding portions of the eye as they normally appear, prior to any surgery or insertion of the iris retractor;

FIG. 4 is a side elevational view of the iris retractor seen in FIG. 2 as it is being inserted into the pupil in its oval configuration;

FIG. 5 is a side elevational view of the iris retractor in its circular form as shown in FIG. 1 after it has been fully inserted into the pupil.

DETAILED DESCRIPTION

In describing the preferred embodiment of the instant invention, reference is made to the drawings, wherein there is seen in FIG. 1 a plastic iris retractor generally designated 10 in a circular configuration. The retractor 10 comprises a ring 12 and an arcuate flange 14 coextensive therewith depending outwardly therefrom. The retractor 10, in its normal condition, is circular, as seen in FIG. 1, but may be compressed into an oval configuration as seen in FIG. 2 as explained hereinbelow.

The retractor 10 also includes a plurality of transverse, reinforcing struts 16 which extend from the ring 12 acress the flange 14. Looking at FIG. 1, the radius of the ring 12 is preferably about 8.5 mm. while the radius of the flange 14 is preferably about 9.0 mm. The reinforcing struts are cirular in cross section and preferably about 0.3 mm. in diameter.

As best seen in FIGS. 1 and 2, the retractor 10 further includes a pair of opposing pinions 18 and 20 co-linear with the center of the ring 12 having openings therein 21 and 23 respectively. In the preferred embodiment, each of the pinions 18 and 20 is about 0.5 mm. in diameter.

Prior to the eye surgery, the anterior portion of the eye appears as seen in FIG. 3, with the cornea 26 completely intact. In order for the surgery to proceed, the cornea 26 must be cut as seen in FIG. 4 to permit insertion of the retractor 10 into the pupil 32. Before the retractor 10 is inserted, a suitably designed pair of forceps 28 engages the openings 21 and 23 in the pinions 18 and 20 respectively (see FIG. 4) in order to contract the retractor 10 into the oval form shown in FIG. 2. Upon insertion of the retractor 10 into the pupil 32, the forceps 28 permit the resiliency of the retractor 10 to expand the retractor 10 back to its original, circular form shown in FIG. 1. The flange 14 of the retractor 10 is thus worked into an abutting relationship with the iris 30, in which the flange 14 holds back the iris 30 and thereby enlarges the pupil 32. The retraction afforded by the retractor 10 allows easy access to the lens 34 and the capsular fornix around the entire circumference of the anterior chamber, thereby reducing the need for additional instrumentation in the eye.

The retractor 10 should be formed from a non-toxic, disposable material, preferably silicone, and is intended for a single use only.

Various modifications and changes are contemplated and may obviously be resorted to, without departing from the spirit or scope of the invention as hereinafter defined by the appended claims.

What is claimed is:

1. An iris retractor for use during eye surgery, comprising:
   a substantially circular, resilient ring, said ring having an arcuate flange co-extensive therewith extending outwardly therefrom;
   a plurality of transverse, reinforcing struts extending from said ring across said arcuate flange; and
   a pair of opposing pinions situated on the flange of the substantially circular, resilient ring and co-linear with the center of said ring, wherein said retractor, prior to being placed within the pupil, may be contracted into a substantially oval configuration by means of suitable forceps engaging said opposing pinions, and wherein said retractor, when placed within the pupil, may be expanded back into its circular configuration by means of the resiliency within said retractor.

2. The iris retractor defined in claim 1, wherein the pair of opposing pinions are each about 0.5 mm. in diameter.

3. The iris retractor defined in claim 1, wherein the radius of the ring is about 8.5 mm.

4. The iris retractor defined in claim 3, wherein the radius of the flange is about 9.0 mm.

5. The iris retractor as defined in claim 1, wherein the entire retractor is formed from a non-toxic, disposable material.

6. The iris retractor as defined in claim 5, wherein the non-toxic, disposable material comprises silicone.